(12) United States Patent
Anderson et al.

(10) Patent No.: US 8,263,384 B2
(45) Date of Patent: Sep. 11, 2012

(54) BIOLOGICAL PRODUCTION OF THYMIDINE

(75) Inventors: David Martin Anderson, Gaithersburg, MD (US); Andrew John Collis, Ulverston (GB); Lin Liu, Gaithersburg, MD (US); Sergey Podkovyrov, Gaithersburg, MD (US); Christopher Preston, Ulverston (GB)

(73) Assignee: Glaxo Group Limited, Greenford, Middlesex (GB)

( * ) Notice: Subject to any disclaimer, the term of this patent is extended or adjusted under 35 U.S.C. 154(b) by 906 days.

(21) Appl. No.: 12/278,227

(22) PCT Filed: Feb. 5, 2007

(86) PCT No.: PCT/EP2007/051072
§ 371 (c)(1),
(2), (4) Date: Aug. 4, 2008

(87) PCT Pub. No.: WO2007/090810
PCT Pub. Date: Aug. 16, 2007

(65) Prior Publication Data
US 2009/0081735 A1    Mar. 26, 2009

(30) Foreign Application Priority Data
Feb. 6, 2006    (GB) .................................. 0602339.4

(51) Int. Cl.
*C12N 1/21*    (2006.01)
*C12P 19/38*    (2006.01)
(52) U.S. Cl. .................. 435/252.3; 435/189; 435/320.1; 435/87
(58) Field of Classification Search .......................... None
See application file for complete search history.

(56) References Cited

U.S. PATENT DOCUMENTS
5,213,972 A * 5/1993 McCandliss et al. ........... 435/89

FOREIGN PATENT DOCUMENTS
WO    WO 91/09130    6/1991
WO    WO 01/02580    1/2001

OTHER PUBLICATIONS

S. Purohit, et al., "Nucleotide Sequence Reveals Overlap between T4 Phage Genes Encoding Dihydrofolate Reductase and Thymidylate Synthase", J. Biological Chem., 259(10): 6261-6266. (1984).*

S. Purohit, et al., Nucleotide Sequence Reveals Overlap between T4 Phage Genes Encoding Dihydrofolate Reductase and Thymidylate Synthase, J. Biological Chem., vol. 259 No. 10, pp. 6261-6266 (1984). XP00247548.

D. R. Appling, et al., Regulation of Expression of the ADE-3 Gene for Yeast C-1 Tetrahydrofolate Synthase A Trifunctional Enzyme Involved in 1 Carbon Metabolism, J. Biological Chem., vol. 260 No. 2, pp. 1248-1256 (1985). XP002437551.

P.D. Ravnikar, et al., Structural and Functional Analysis of a Cloned Segment of *Escherichia-Coli* DNA That Specifies Proteins of a 4-Carbon Pathway of Serine Biosynthesis, J. Bacteriology, vol. 169 No. 10, pp. 4716-4721 (1987). XP002437550.

C. W. Carreras, et al., The Catalytic Mechanism and Structure of Thymidylate Synthase, Annual Review of Biochemistry, vol. 64, pp. 721-762 (1995). XP002093507.

M.A. Bernard, Metabolic Functions of Microbial Nucleoside Diphosphate Kinases, J. Bioenergetics & Biomembranes, vol. 32, No. 3, pp. 259-267 (2000). XP002437624.

H. Myllykallio, et al., Life without dihydrofolate reductase FoIA, Trends in Microbiology, vol. 11 No. 5, p. 220-223 (2003). XP002437549.

H. C. Lee, et al., Overproduction of thymidine by recombinant Brevibacterium helvolum amplified with thymidine monophosphate phosphohydrolase gene from bacteriophage PBS2, Biotechnology Letters, vol. 26, pp. 265-268 (2004). XP002437552.

EP Office Action dated Feb. 27, 2009.
EP Office Action dated Nov. 24, 2009.
EP Office Action dated Jun. 29, 2010.
EP Office Action dated Apr. 1, 2011.

* cited by examiner

*Primary Examiner* — Rebecca E. Prouty
(74) *Attorney, Agent, or Firm* — Michael M. Conger (57) ABSTRACT

Novel organisms, including DNA construct host cell combinations, are disclosed. The organisms comprise a transcription unit (e.g. operon) comprising DNA sequences encoding for enzymes which promote the supply of single carbon units for the conversion of dUMP to dTMP. Examples include: dihydrofolate reductase genes e.g. T4 frd; Serine Hydroxymethyltransferase genes e.g. glyA; 3-phosphoglycerate dehydrogenase genes e.g. serA; and THF synthase genes e.g. ADE3. The organisms are used in a biological method of producing thymidine with significantly reduced levels of uridine.

5 Claims, 9 Drawing Sheets

Figure 1: Thymidine Biosynthesis in *Escherichia coli* K12

Figure 2: Thymidylate Synthase Reactions dUMP  deoxyuridylic acid
dTMP  thymidylic acid
CH$_2$-THF  5,10-methylenetetrahydrofolate
THF  tetrahydrofolate
DHF  dihydrofolate
NADPH  reduced nicotinamide adenine dinucleotide
NAD  nicotinamide adenine dinucleotide
FADH$_2$  reduced flavin adenine dinucleotide
FAD  flavin adenine dinucleotide Figure 3: Regeneration of $CH_2$-THF through Serine and Glycine Figure 4: Regeneration of CH$_2$-THF from Formate Figure 5: Genetic Targets to Improve $CH_2$-THF Regeneration

Figure 6: pCG532

Figure 7: pCG609

Figure 8: pCG376

Figure 9: Thymidine Production in Various Strains/ Constructs

US 8,263,384 B2

BIOLOGICAL PRODUCTION OF THYMIDINE

This application is filed pursuant to 35 U.S.C. §371 as a United States National Phase Application of International Patent Application Ser. No. PCT/EP2007/051072 filed Feb. 5, 2007, which claims priority from Great Britain Application No. 0602339.4 filed in the United Kingdom on Feb. 6, 2006, the content of which is incorporated herein by reference.

FIELD OF THE INVENTION

The present invention relates to the biological production of thymidine. More particularly it relates to a method utilizing genetically manipulated biological materials. The genetically manipulated biological materials may include a thymidine producing organism, such as a bacterium or one or more DNA constructs, for example plasmids, which in combination with a suitable host cell will, when grown in an appropriate culture media, give rise to the biological production of thymidine.

BACKGROUND OF THE INVENTION

The pyrimidine deoxyribonucleoside thymidine is useful as a pharmaceutical intermediate. It is particular important for the chemical synthesis of the AZT, also known as zidovidine or azidothymidine. This is an antiretroviral drug of the nucleoside reverse transcriptase inhibitor (NRTI) class, which, under the trademark Retrovir, was the first drug licensed to treat HIV infection.

HIV/AIDS is usually treated with combinations of three or more antiretroviral drugs (De Clercq, Med. Chem. Res. 13: 439-478, 2004). AZT has an important and expanded role as a major component of combination therapies and is sold under a variety of trademarks including Retrovir, Zidovir, Viro-Z, Aviro-Z and Zido-H.

AZT is particularly valuable when combined with the NRTI drug 3TC (lamivudine). These two drugs are available, formulated in a single pill, under the trademarks Combivir and Duovir. A triple NRTI combination of AZT, 3TC and abacavir is sold under the trademark Trizivir. Other NRTI drugs used in conjunction with AZT include didanosine, emtricitabine and zalcitabine.

AZT is also useful in combination with HIV protease inhibitor drugs including amprenavir, atazanavir, indinavir, ritonavir and saquinavir, and with non-nucleoside reverse transcriptase inhibitors (NNRTI) including delavirdine, efavirenz and nevirapine.

AZT is the only anti-HIV drug approved for use during pregnancy (Lyall, et al., HIV Med. 2: 314-334, 2001). In 1997 about 600,000 children died of AIDS contracted by mother to baby transmission. AZT, taken in the last trimester of pregnancy, may reduce the risk of viral transmission by 67% (Mitchla & Sharland, Expert Opin. Pharmacother. 1: 239-248, 2000).

Fermentation technology is an attractive alternative to chemical synthesis for commercial preparation of the large quantities of thymidine required for AZT manufacture. Fermentation processes are well established in industry as a means to produce biological molecules such as antibiotics, amino acids and vitamins at large scale and relatively low cost (Atkinson, & Mavituna, Biochemical Engineering and Biotechnology Handbook, 2nd Edition, New York, Stockton Press, 1991).

However thymidine is not usually found in its "free" form in nature, but produced as the monophosphate thymidylic acid and incorporated into DNA as the triphosphate. Biological systems do not naturally produce significant amounts of thymidine, hence a mutant or engineered organism is required.

In EP 0,344,937 there are disclosed strains of Brevibacterium selected to produce thymidine on aerobic cultivation. Reference is also made to a Japanese patent publication No. 39-16345, which teaches the use of a mutant strain of Bacillus subtlis in the fermentative production of a polysaccharide containing thymidine.

In U.S. Pat. No. 5,213,972 (McCandliss & Anderson), the entire contents of which are incorporated herein by reference and to which the reader is specifically referred, a process is disclosed for the production of pyrimidine deoxyribonucleosides (PdN) such as thymidine and 2'-deoxyuridine. A replicatable microorganism is taught, incorporating and expressing a DNA sequence encoding a PdN phosphohydrolase that converts a PdN monophosphate to a PdN.

More particularly, McCandliss & Anderson, supra, describe a fermentation method that can be used to produce thymidine that involves the expression of deoxythymidylate phosphohydrolase (dTMPase) from the Bacillus subtlis bacteriophage PBS1. This type of enzyme is found in nature expressed by bacteriophages that incorporate PdNs such as 2'-deoxyuridine or 5-hydroxymethyl-2'-deoxyuridine in their DNA in place of thymidine.

In the thymidine fermentation described in U.S. Pat. No. 5,213,972 the enzymes that degrade thymidine, (thymidine phosphorylase and uridine phosphorylase), have been removed by mutation so that thymidine accumulates. Thus, the use of the dTMPase enzyme helps create the pathway to allow thymidine synthesis. An expression of dTMPase alone, however, may not assure a commercially viable level of thymidine production In WO 01/02580, the entire contents of which are also incorporated herein by reference and to which the reader is also specifically referred, there are described improvements which result in the enhanced production of thymidine by cells expressing dTMPase.

However a problem in the manufacture of biologically produced thymidine lies in the concomitant production of 2'-deoxyuridine (UdR) in the fermentation process. The two molecules have similar properties, differing in structure by a single methyl group, and separation during downstream processing is difficult and expensive. For a pharmaceutical application, such as the synthesis of AZT, high purity thymidine may be required with low levels of UdR.

It would be beneficial if thymidine biologically produced by fermentation gave significantly reduced levels of UdR compared to current processes, such that the requirement for downstream purification to remove this material were minimised or eliminated.

By significantly reduced is meant that (contaminating) levels of UdR constitute less than 25%, more preferably still less than 10%, more preferably still less than 5% through 4%, 3%, and 2%, to levels of 1% and less in the fermented thymidine product.

Ideally, "high" levels of thymidine should be attained. Levels of thymidine can be given as "specific productivity" figures where the measure is determined 4-6 hours after induction. Levels of greater than 5 mg TdR/1/hr/g dry cell weight, more particularly greater than 10 mg TdR/1/hr/g dry cell weight and more preferably specific productivity figures of greater than 15 through 20 and 25 are preferred.

These levels should most preferably be obtained with the reduced levels of UdR described above and thus the figures can be combined such that, for example a TdR titre of 5 g/l might be obtained containing less than, for example 5% UdR.

Indeed the prior art process, using the plasmid pCG532 in host strain CMG2451, as disclosed in WO 01/02580, produces an average UdR content in shake flask tests of 34.5%. At such high levels downstream processing to separate thymidine from UdR is difficult and costly.

It is an aim of the present invention to modify thymidine producing organisms such that they produce thymidine without significant concomitant production of UdR.

As used herein the term "organism" includes an organism which can produce thymidine through expression of DNA encoded in its chromosome (as disclosed in, for example, EP 0344937) or DNA which it hosts (as disclosed in, for example, U.S. Pat. No. 5,213,972 and WO 01/02580). This host DNA may be present as one or more DNA constructs, such as, for example, one or more plasmids.

In particular it is an aim to provide an improvement in the quality of thymidine produced as compared to the construct/host combination disclosed in WO 01/02580.

It is a further aim to ensure that any gene modification made to a construct is stable such that when the construct is introduced into a host cell, and the combination grown, the host is unable to propagate itself without the construct being present. i.e. if the construct is lost, the organism dies.

SUMMARY OF THE INVENTION

Unexpectedly, it has been found that there is a significant rate limiting step in the production of thymidine which occurs around the conversion of dUMP to dTMP, such that dUMP may be simultaneously directed towards the production of UdR. This limitation cannot be relieved by simple overexpression of the enzyme thymidylate synthase, which catalyses the conversion reaction. However, by ensuring the availability of a ready supply of donor methyl groups the applicant has determined that thymidine can be produced with a significant reduction in the levels of contaminating UdR, (from around 35% to less than 5% and in some cases less than 1%).

In accordance with a first aspect of the present invention there is provided an organism capable of producing thymidine when grown in a culture medium, the organism comprising one or more genetic modification to its DNA, or some extra-chromosomal DNA necessary for its growth, characterized in that the organism comprises one or more genetic modifications which result in the thymidine biosynthetic pathway preferentially producing TdR at the expense of UdR as a consequence of one or more genetic modifications which increase the availability of a single carbon unit for conversion of dUMP to dTMP.

The one or more modifications are preferably modifications which increase the amount of 5,10-methylenetetrahydrofolate ($CH_2$-THF) available to thymidylate synthase for conversion of dUMP to dTMP. $CH_2$-THF is a common one-carbon unit donor for both known classes of thymidylate synthase (EC 2.1.1.45 and EC 2.1.1.148). The reactions catalysed by these two enzymes are compared in FIG. 2.

In the majority of cases the hydrogen atoms required to reduce the methylene group of the donor molecule to a methyl group are provided by $CH_2$-THF itself, so that conversion of dUMP to dTMP requires concurrent conversion of $CH_2$-THF to dihydrofolate (DHF). This form of the enzyme is designated EC 2.1.1.45 and is encoded by, for example, the thyA gene of E. coli or the td gene of bacteriophage T4.

In an alternative form of the enzyme designated EC 2.1.1.148 and encoded, for example by the thyX gene of Helicobacter pylori, two hydrogen atoms are provided by the reduced form of a flavin nucleotide such as flavin adenine dinucleotide (FAD). In this case $CH_2$-THF is converted to tetrahydrofolate (THF) and $FADH_2$ to FAD in the thymidylate synthase reaction (Myllykallio, H. et al., Science 297: 105-107, 2002).

$CH_2$-THF is normally regenerated by transfer of a one-carbon unit to THF. In an organism utilizing the EC 2.1.1.45 thymidylate synthase there must be, as a first step, conversion of DHF to THF by the action of a dihydrofolate reductase (EC 1.1.5.3), expressed for example by an E. coli folA gene or a T4 frd gene. With the EC 2.1.1.148 form of thymidylate synthase this step is not required.

Figure 3:
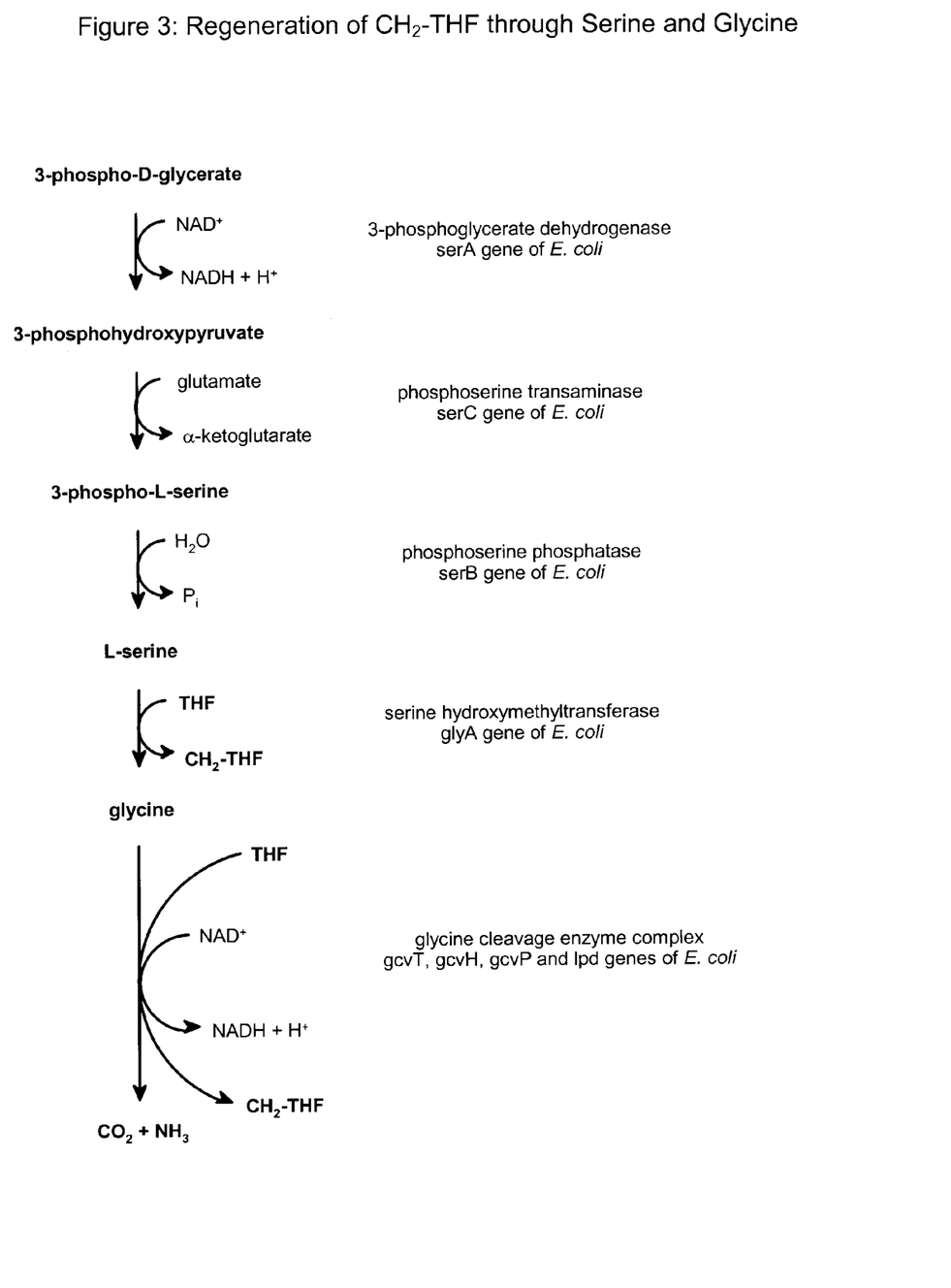
FIG. 3 illustrates regeneration of $CH_2$-THF from L-serine and glycine.

The primary metabolic route to generate $CH_2$-THF from THF is a pathway through the amino acids serine and glycine, starting from 3-phosphoglycerate, which is an intermediate in carbohydrate metabolism. This serine-glycine-$C_1$ pathway is shown in FIG. 3. The first committed step is the generation of 3-phosphohydroxypyruvate by action of phosphoglycerate dehydrogenase encoded by, for example, the serA gene of E. coli.

$CH_2$-THF is generated at two steps in this pathway: the first is the conversion of L-serine to glycine by the action of serine hydroxymethyltransferase encoded by, for example, the E. coli glyA gene. The second is the conversion of glycine to carbon dioxide and ammonia by the glycine cleavage enzyme complex that is the product of at least four genes.

Figure 4:
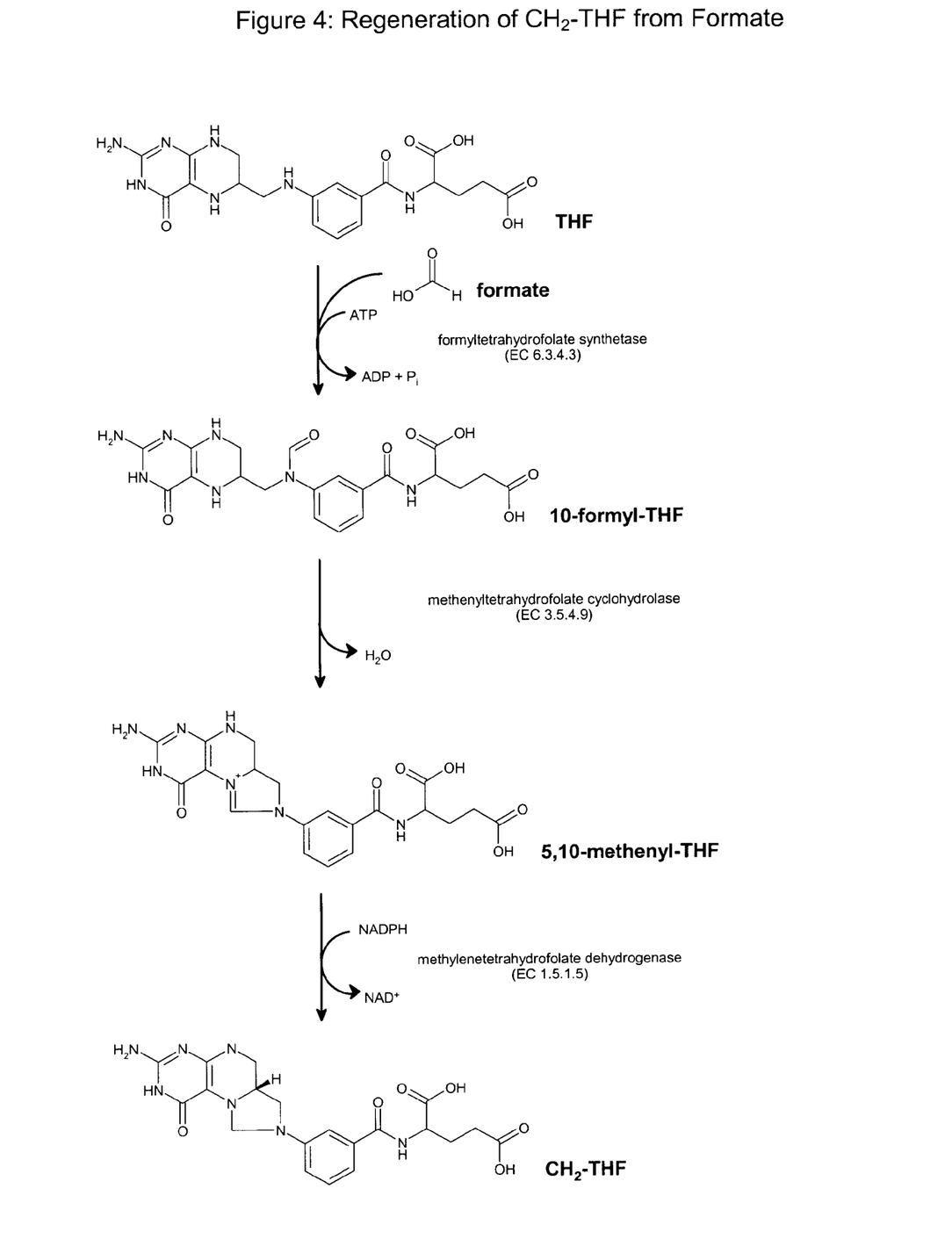
FIG. 4 illustrates regeneration of $CH_2$-THF from formate.

In many organisms $CH_2$-THF can also be generated from THF in three steps using formate to provide the carbon atom, as shown in FIG. 4. Formate can be derived from the central metabolic intermediate pyruvate. In eukaryotic organisms the three required enzyme activities may be present in a single trifunctional protein, as encoded for example by the ADE3 gene of the yeast Saccharomyces cerevisiae.

Gene modifications of chromosomal or extra-chromosomal DNA in thymidine producing organisms which promote the availability of $CH_2$-THF have lead to the production of thymidine in good yield with significantly reduced levels of UdR. Gene modifications of this type can be used to reverse an increase in UdR that may result when total PdN production is increased using genetic manipulations as taught in U.S. Pat. No. 5,213,972 and WO 01/02580, thus allowing for process yield improvement without unacceptable increase in UdR impurity.

Preferably, but by no means essentially, the organism is a bacterium, more preferably E. coli. However, Brevibacterium and Bacillus species, as disclosed in the prior art documents identified previously, and other thymidine producing organisms e.g. the bacterium Corynebacterium or yeast could be selected and modified in accordance with the described invention. It will be appreciated that there are various modes by which the availability of $CH_2$-THF may be increased in a thymidine-producing organism, and that the most effective will in each case depend upon the genetic background of that organism.

The organism will preferably also comprise a transcriptional unit (which may be chromosomal or extra-chromosomal) capable of over-expressing a thymidylate synthase encoded by, for example, a td or thyA gene, and one or more genes which cause thymidine to be produced from dTMP, such as, for example, a deoxythymidylate phosphohydrolase encoded by, for example, a dTMPase gene.

In the favored embodiment, where thymidylate synthase is of the EC 2.1.1.45 type generating DHF, the organism includes a gene which, when expressed, facilitates the conversion of DHF to THF. This may be a dihydrofolate reductase gene such as folA or frd. The preferred dihydrofolate reductase gene is a bacteriophage gene, more preferably a T even phage gene, and most preferably the T4 bacteriophage gene frd.

The dihydrofolate reductase gene may be introduced directly into the organism's chromosomal DNA or incorporated into a DNA construct which may in turn be hosted by the organism. Preferably the DNA construct is a vector, such as a plasmid, virus, transposon, or mini-chromosome.

Where a DNA construct is used to introduce the DNA into a host cell it is preferable to ensure it is designed to be stably maintained in its intended host.

In a particularly favoured embodiment and best mode the organism is *E. coli* host strain CMG2576, derived from strain CMG2451 disclosed in WO 01/02580, harbouring plasmid pCG609, derived from pCG532 disclosed in WO 01/02580. Fuller details of their make up are given in Examples 3 and 4. This combination has been doubly stabilised to ensure that the plasmid is maintained within the host strain during growth under "non-inducing" conditions.

The TMPase gene is inserted into the host chromosome, coupled with a bacteriophage lambda $P_L$ promoter. The plasmid carries a bacteriophage lambda $cI_{857}$ temperature sensitive repressor under control of its own promoter, relocated from the chromosome in the host strains disclosed in WO 01/02580. If the plasmid is lost there is no repressor made, and the TMPase gene is expressed so that TMP is converted to thymidine and the organism dies.

The applicants determined that this stabilization mechanism was insufficient for use in large scale cultures with the many generations of growth required, since plasmid loss accompanied by simultaneous inactivation of the chromosomally located TMPase gene is an event sufficiently frequent to allow the growth of plasmid-less derivatives. A second stabilization mechanism was added, where a gene essential for growth and survival was deleted from the chromosome and relocated to the plasmid. In the CMG2576 and pCG609 combination this gene is ThyA, cloned into the plasmid under control of a lac promoter.

Without a functional ThyA gene, the cell cannot make TMP, hence cannot make TTP for synthesis of DNA and dies. This mechanism is particularly effective because genes can readily mutate to lose a function, but much less readily recreate one that is completely lost. Furthermore, the product of the missing enzyme is a phosphorylated compound that is unable to "cross-feed" by passing out of functional cells and into those having lost the plasmid-borne gene.

In order to demonstrate the more general aspects of the invention further examples, not always directly comparable, are described in the detailed description. The shake flask test data often includes the introduction of a "test gene" in a second plasmid. However such multi plasmid systems have not been subjected to scale testing and their genetic stability on large-scale culture has not been determined.

According to a second aspect of the present invention there is provided a method of producing thymidine comprising growing an organism in a culture medium, the organism comprising one or more genetic modification to its DNA, or some extra-chromosomal DNA necessary for its growth, characterized in that the organism comprises one or more genetic modifications which result in the thymidine biosynthetic pathway preferentially producing TdR at the expense of UdR as a consequence of one or more genetic modifications which increase the availability of single carbon units for conversion of dUMP to dTMP.

Preferably the UdR content is less than 5% of the thymidine content.

Preferably the thymidine content, by way of specific productivity, is greater than 5 mg TdR/1/hr/g dry cell weight, more preferably greater than 7.5 through 10 in steps of 2.5 to 25 mg TdR/1/hr/g dry cell weight and higher.

According to a third aspect of the present invention there is provided culture medium capable of supporting growth and thymidine production for an organism of the invention.

According to yet a further aspect of the present invention there is provided zidovidine manufactured from thymidine produced according to the method of the invention.

Preferred Embodiments Of The Invention

In a first, and preferred, embodiment a gene is introduced into the organism indirectly as extra-chromosomal DNA, most preferably in the form of a plasmid (rather than directly into the chromosome). The preferred gene is one which expresses an enzyme which is able to ensure that a thymidylate synthase enzyme (e.g. EC 2.1.1.45, EC 2.1.1.148), which converts deoxyuridine monophosphate (dUMP) to thymidine monophosphate (dTMP), is provided with a ready supply of methyl groups such that the majority of dUMP is methylated to dTMP as opposed to being converted to 2'-deoxyuridine (UdR).

In this preferred embodiment the favoured thymidylate synthase enzyme is of the EC 2.1.1.45 type and the favoured gene is one which aids the conversion of dihydrofolate (DHF) to tetrahydrofolate (THF). A suitable gene is a gene encoding dihydrofolate reductase. This may be a wild type or deregulated bacterial gene or a bacteriophage gene. A particular favoured gene, and one used to exemplify the invention, is the frd gene of bacteriophage T4 (T4frd).

In alternative embodiments gene modifications are made to aid the conversion of THF to 5,10-methylenetetrahydrofolate ($CH_2$-THF). All of these genetic modifications have the common goal of forcing conversion of dUMP to dTMP in preference to UdR.

Gene modifications which have been shown to work either as an alternative to the preferred modification or in combination therewith include the following:

Making a modification to an enzyme that directly effects the conversion of THF to $CH_2$-THF. One such modification is the introduction of a gene expressing the enzyme serine hydroxymethyltransferase, which converts L-serine to glycine and at the same time catalyses conversion of THF to $CH_2$-THF for example, glyA of *E. coli*. Further such modifications would include the introduction of a gene or genes expressing one or more components of the glycine cleavage enzyme complex that catalyses conversion of THF to $CH_2$-THF concurrent with the conversion of glycine to carbon dioxide and ammonia, for example the gcvT, gcvH, gcvP and lpd genes of *E. coli*.

Making a gene modification which directly effects conversion of THF to $CH_2$-THF using formate to provide the required one-carbon unit. One such modification is the introduction of a gene or genes expressing the enzyme activities formyl-THF synthase, methenyl-THF cyclohydrolase and $CH_3$-THF dehydrogenase. One example would be the yeast ADE3 gene that encodes a trifunctional protein with all of these activities. A further example would be the introduction into *E. coli* of a gene encoding just the formyl-THF synthase, the other enzymes required for this conversion being present already.

Making a gene modification that increases the availability of a substrate for a reaction that effects conversion of THF to $CH_2$-THF. One such case is the promotion of availability of L-serine as substrate for serine hydroxymethyltransferase through introduction of a gene such as *E. Coli* serA expressing 3-phosphoglycerate dehydrogenase, which catalyses the first step in the pathway from carbohydrate to L-serine. Further examples would include the introduction of genes expressing the later enzymes involved in the generation of L-serine from 3-phospho-D-glycerate, such as serC and serB of *E. coli*, or any gene modification that increases the availability of formate to the enzyme complex encoded by the yeast ADE3 gene.

The respective aspects of the present invention give rise to a significant advance over the teachings of both U.S. Pat. No. 5,213,972 and WO 01/02580 and provide improved DNA constructs and host cells comprising the constructs for use in the commercial production of thymidine. They can also be applied to the modification of other thymidine producing organisms.

Other objects, features and advantages of the present invention will become apparent from the following description. It should be understood, however, that these represent preferred embodiments of the invention and are by way of illustration only. Various modifications and changes within the spirit and scope of the invention will become apparent to those skilled in the art.

The constructs of the present invention may be chromosomal or more preferably extra-chromosomal e.g. located on a vector.

Vectors of the present invention include plasmid, virus (including phage), transposons, and mini-chromosomes, preferably plasmids.

The vector may be introduced into a host cell according to any convenient method known to those skilled in the art, e.g. P1 transduction, electroporation or transformation.

Suitable host cells useful in the present invention include eukaryotes (e.g. fungi) and prokaryotes (e.g. bacteria). Prokaryotes include *E. coli, Salmonella, Pseudomonas, Brevibacterium, Bacillus*, strains and mutants thereof.

Vectors of the present invention preferably comprise a regulatory element (e.g. promoter such as lambda $P_L$, operator, activator, repressor such as lambda repressor, particularly a temperature sensitive variant, and/or enhancer), appropriate termination sequences, initiation sequences and ribosome binding sites. The vector may further comprise a selectable marker. Alternatively, regulatory elements (particularly lambda repressor) may be located on the host cell chromosome.

Host cells modified according to the present invention are particularly useful in the commercial production of thymidine. In a particularly advantageous use of the present invention, *E. coli* host cells comprising (harboring or incorporating) a plasmid modified according to the present invention (particularly in conjunction with the teachings of U.S. Pat. No. 5,213,972 or WO 01/02580) may be used in the commercial production of thymidine. Thus, host cells modified according to the present invention may further comprise dTMPase derived from e.g. PBS1 and the mutations taught in U.S. Pat. No. 5,213,972, e.g. deoA, tdk-1 and udp-1, along with the further improvements to the construct taught in WO 01/02580, e.g. T4 nrdCAB, T4 td, dcd, and udk.

Generally, a fermentation method is employed as taught in WO 01/02580, which involves submerging the cells in a culture medium contained within a suitable vessel. Following culturing under appropriate conditions, produced thymidine is harvested and purified (enriched), if necessary, to pharmaceutical grade according to standard protocols. The purified thymidine may then be used in the production of medicaments, e.g. pharmaceutical compositions such as AZT.

BRIEF DESCRIPTION OF THE DRAWINGS

The present invention is illustrated, by way of example only, with reference to the following figures in which.

DETAILED DESCRIPTION

Figure 1:
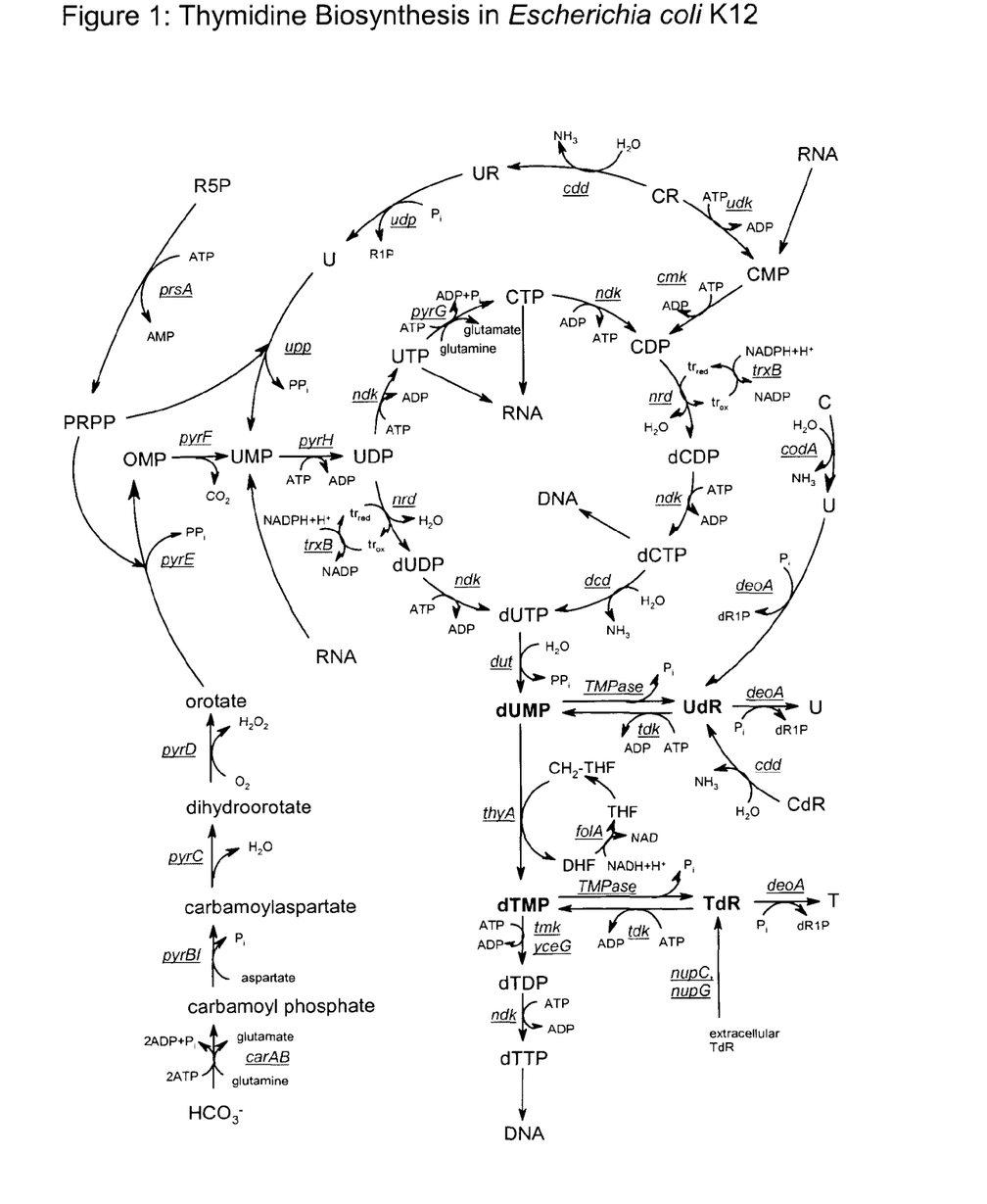
FIG. 1 illustrates a thymidine biosynthesis pathway.

FIG. 1 illustrates the complexity of the thymidine biosynthetic pathway and the associated genetics, using as an example *E. coli* K12 with the addition of a TMPase gene. Thymidine is TdR and 2'-deoxyuridine is UdR, at the lower right hand side of the diagram. UdR differs chemically from TdR by the absence of a single methyl group. The structural similarity between the compounds makes purification difficult and costly. The invention concerns itself with making gene modifications which influence the preferential formation of TdR at the expense of the production of UdR.

The applicant has determined that the levels of TdR relative to UdR can be effectively controlled by ensuring that the process step dUMP to dTMP, catalysed by expression of e.g. thymidylate synthase from a thymidylate synthase gene (e.g. td, thyA or thyX), is provided with an increased supply of one-carbon units as e.g. $CH_2$-THF.

Figure 2:
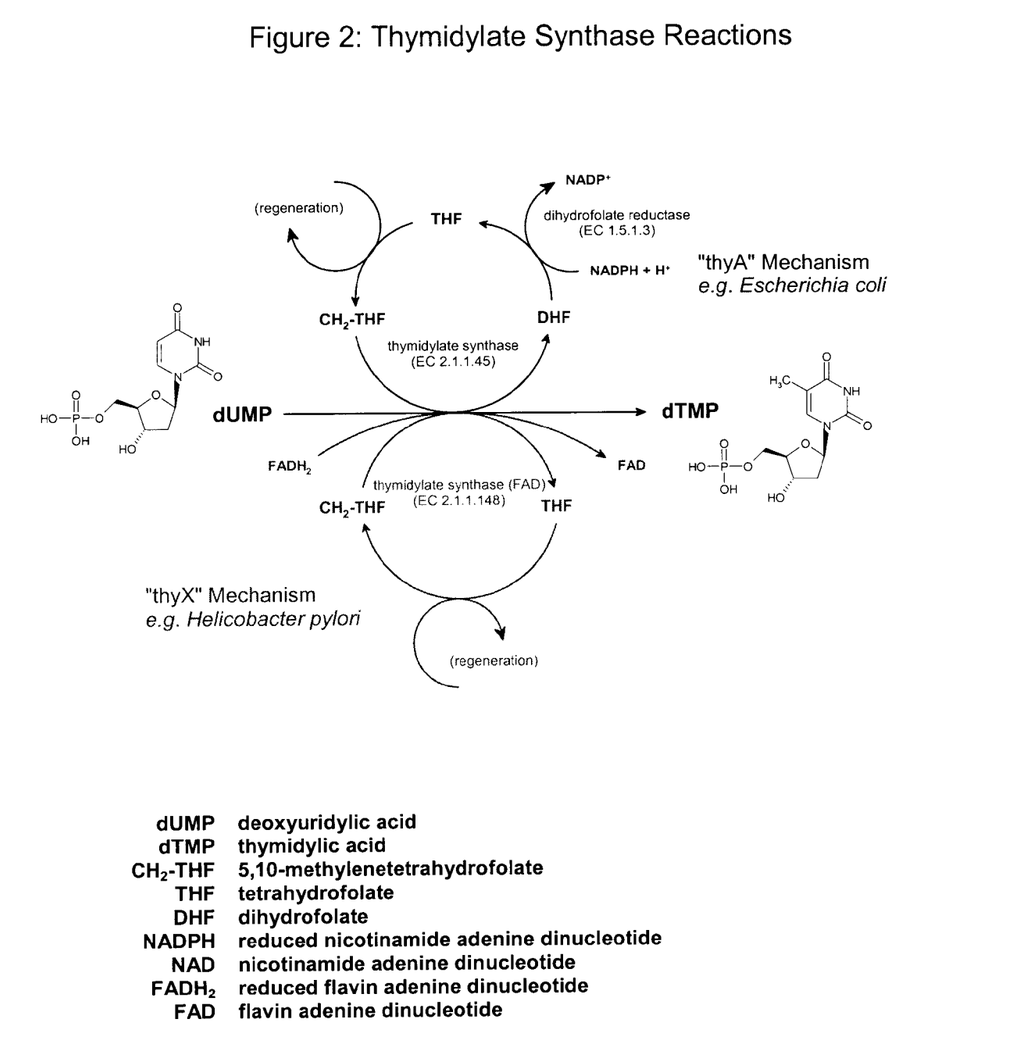
FIG. 2 illustrates the thymidylate synthase reaction (converting dUMP to dTMP)

This is primarily achieved by ensuring the depleted one-carbon donor molecule produced by the conversion of dUMP to dTMP is rapidly recycled to its active state as $CH_2$-THF. FIG. 2 shows two alternative mechanisms for thymidylate synthase, each producing a different depleted one-carbon donor. Where thymidylate synthase is of the type EC 2.1.1.45, encoded for example by a thyA or td gene, the depleted donor is DHF. When the enzyme is of the EC 2.1.1.148 type, encoded for example by a thyX gene, the depleted donor is THF.

Because the direct precursor of $CH_2$-THF is THF, it will be apparent that in an organism using the EC 2.1.1.45 thymidylate synthase, *E. coli* for example, the first step must be conversion of DHF to THF. By introducing into such an organism a dihydrofolate reductase gene, encoding an enzyme that catalyses this conversion, the applicant has been able to significantly reduce the levels of contaminating UdR and additionally increase thymidine productivity as is illustrated in Example 6.

This approach allows for further improvement of thymidine fermentation process yields according to the principles taught by U.S. Pat. No. 5,213,972 and/or WO 01/02580. Where previously genetic modifications to increase total pyrimidine deoxyribonucleosides would have resulted primarily in increased levels of UdR, by introducing a dihydrofolate reductase gene this additional product can now be directed to TdR as illustrated by Example 7.

In Example 8 this approach has been combined with further modifications to ensure that a plasmid construct carrying the dihydrofolate reductase and other cloned genes required for TdR production is stably maintained in its appropriate *E. coli* host strain. This represents the current best mode improvement over the prior art process taught by WO 01/02580, but by no means reaches the limit of what may be expected from the present invention.

It will be apparent from FIG. 2 that increasing the conversion of DHF to THF through the introduction of a dihydrofolate reductase gene is one genetic modification that can be made to produce the desired increase in regeneration of $CH_2$-THF in a thymidine producing organism. However, this approach is not applicable for organisms with the type EC 2.1.1.148 thymidylate synthase. In such cases, as in cases where the conversion of DHF to THF is not, or is no longer, the limiting step in regeneration of $CH_2$-THF, there are various alternative or additional genetic modifications that may be applied to achieve the desired outcome of TdR production with low levels of UdR.

Figure 5:
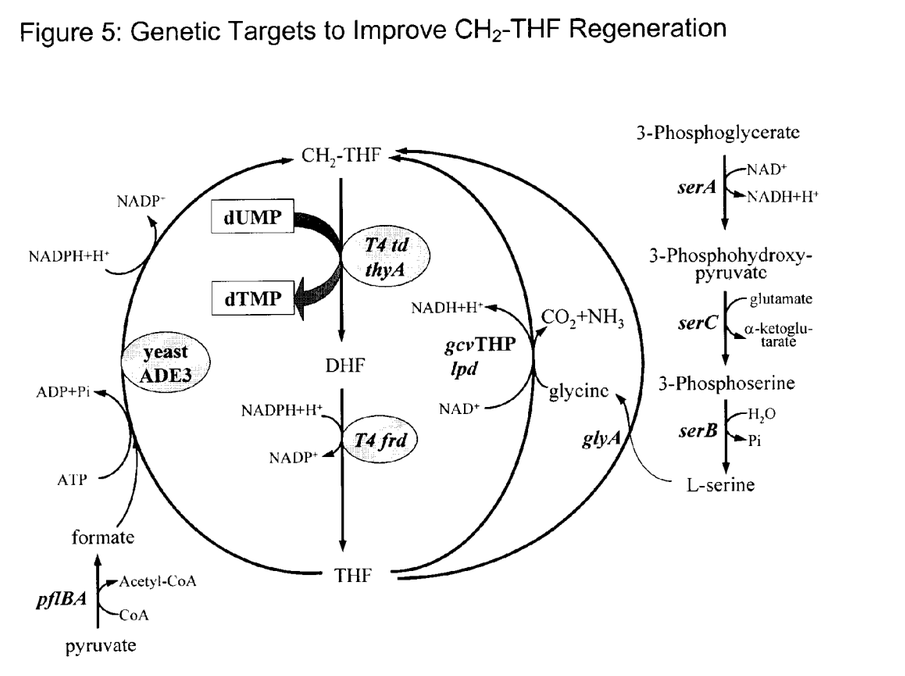
FIG. 5 summarises approaches to improve regeneration of $CH_2$-THF.

Such alternative modifications will become apparent by considering the routes by which THF is biologically converted to $CH_2$-THF, for example through L-serine and glycine as shown in FIG. 3, or through formate as shown in FIG. 4. A variety of possible solutions is summarized in FIG. 5. In general, suitable modifications will either increase the overall rate of synthesis of $CH_2$-THF or improve the rate of supply of one-carbon units to convert THF to $CH_2$-THF.

The applicants have tested a number of examples of these approaches. In Example 9 an enzyme is overexpressed, capable of converting THF to $CH_2$-THF through conversion of L-serine to glycine. In Example 10 another enzyme is overexpressed with the aim of improving the supply of one-carbon units for conversion of THF to $CH_2$-THF by increasing the flow of metabolites into the serine/glycine pathway shown in FIG. 3. Examples 11 and 12 use different methods to introduce into *E. coli* a non-native pathway for conversion of THF to $CH_2$-THF using formate as one-carbon donor.

In each case there is either i) a small decrease in UdR level, ii) a small increase in TdR without relative increase in UdR, or iii) a combination of both. Compared with the effects of adding dihydrofolate reductase shown in Examples 6, 7 and 8, improvements are relatively minor, but it will be appreciated that each could be more significant in an alternative or further improved thymidine-producing organism and is therefore a valid example of the current invention.

EXAMPLE 1 (Comparative)

Prior Art Construct/Strain

Figure 6:
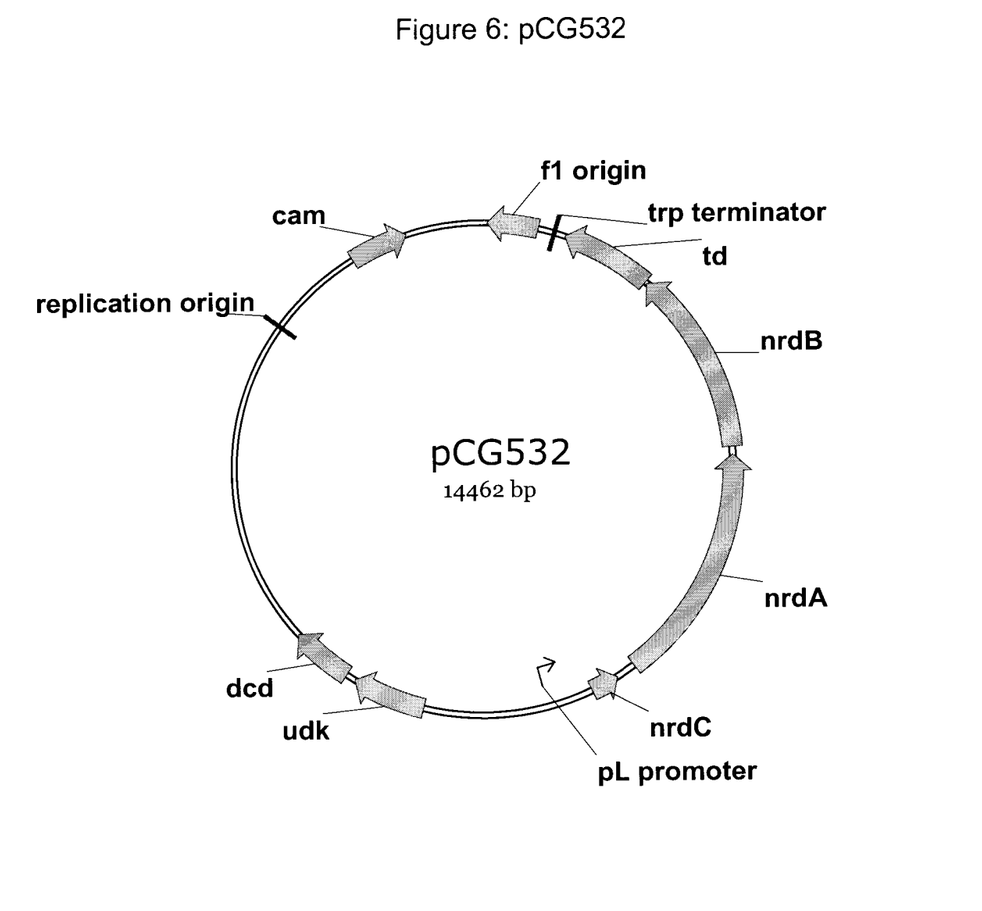
FIG. 6 illustrates a map for plasmid pCG532 (the prior art teaching)

The benefits of the present invention will be demonstrated using the prior art construct/strain disclosed in WO 01/02580 as the comparator. FIG. 6 illustrates the construct pCG532 and Table 1 gives the genotype of the *E. coli* host strain CMG2451. It will however be appreciated that not all the genes disclosed therein form an essential part of the present invention, although the presence of a thymidylate synthase gene (td, on the plasmid) and a TMPase (integrated into the chromosome) are important to the preferred embodiment thereof.

TABLE 1

Genotype of Prior Art Host Strain CMG2451

| Strain | Genotype |
|---|---|
| CMG2451 | hsdR-2 supE thi deoA-75 tdk-1 ($\lambda$ $cI_{857}$ $\Delta$BAM $\Delta$H1) nic bio $\Delta$(chlD-pgl) nadA-50::Tn10 udp-1 chr::Tn5::dTMPase $AZT^R$ $FUdR^R$ |

EXAMPLE 2

Shake-Flask Test for Thymidine Production

The construct and strain referred to in Example 1 were grown in culture medium (Table 2) according to the following methodology. Data were obtained for comparative purposes on both the rate of TdR production and the relative amount of UdR impurity (expressed as a percentage of TdR).

All experiments were conducted in 250 mL baffled shake flasks with seven to twelve flasks per tested strain. A fresh seed culture grown in LB medium was used to inoculate 20 mL of medium per flask with about 2.5% volume. Cultures were grown at 31° C. until OD 600 nm=5. The temperature was then shifted from 35.7° to 36.8° C. by moving the flasks to a different shaker. Samples were taken for analysis at 4 to 6 hours post temperature induction.

TABLE 2

Enriched Shake Flask Medium Formulation

| Component | Quantity g/L |
|---|---|
| Potassium phosphate, dibasic | 8.0 |
| Potassium phosphate, monobasic | 8.0 |
| Magnesium sulfate, heptahydrate | 0.4 |
| Ammonium Sulfate | 2.0 |
| Citric acid, trisodium dihydrate | 0.5 |
| Amberex 695, Sensient or Hy-Yest 412, Quest | 10 |
| Amberferm 4015 AG, Sensient | 5-10 |
| Sorbitol | 20 |
| Calcium Carbonate | 10 |
| Trace elements 1000X solution | 1 mL |
| Phenol red | 0.024 |

Medium was adjusted to pH 7.0 with NaOH before autoclaving at 121° C. for 25 minutes. After cooling biotin (1 mg/L final concentration), thiamine (10 mg/L) and nicotinic acid (10 mg/L) were added along with optional antibiotics as needed, ampicillin (100 mg/L), chloramphenicol (30 mg/L), kanamycin (15 mg/L) and tetracycline (25 mg/L). The results are illustrated in Table 3.

TABLE 3

Average Specific Productivity (mg TdR/L/hr./g dry cell weight) for strains in enriched medium

| Host Strain | Plasmid | Specific Productivity | % UdR | Comment |
|---|---|---|---|---|
| CMG2451 | pCG532 | 8.92 | 34.5 | Average of 23 Experiments |

EXAMPLE 3

Development of Improved Host *E. coli* Strain CMG2576 from CMG2451

The host strain was modified through a series of steps as listed in Table 4 below. There were three significant changes overall, although it will be appreciated that none of these form an essential part of the present invention. In the Examples below, intermediate strains CMG2549 and CMG2560 as well as final strain CMG2576 are used to demonstrate aspects of the invention.

Strain CMG2549 differs from CMG2451 in that the chromosomal ndk gene has been knocked out by replacement with an insertionally inactivated ndk::kan. This change was made to improve the overall production of pyrimidine nucleosides according to the principles taught by U.S. Pat. No. 5,213,972 and is important to the demonstration of the utility of the present invention detailed in Example 7.

CMG2560 was constructed by eliminating a lambda prophage from the chromosome, at the same time repairing mutations causing requirements for biotin and nicotinic acid. This change was made in the presence of a plasmid carrying a lambda $cI_{857}$ temperature sensitive repressor, without which the dTMPase gene, inserted into the chromosome and expressed from a lambda $P_L$ promoter, would be active and the organism would degrade dTMP, be unable to make DNA and die.

Finally, CMG2576 differs from CMG2560 in that the chromosomal thyA gene has been replaced with an insertionally inactivated thyA748::Tn10. This change was made in the presence of a plasmid carrying both a lambda $cI_{875}$ repressor and a cloned thyA. Without the plasmid-borne thyA gene the organism is unable to synthesize dTMP, thus unable to make DNA and dies.

The reasons for the changes made to remove the chromosomally located lambda repressor and inactivate the host thyA gene are given in Example 8.

TABLE 4

Derivation of Improved Host E. coli Strain CMG2576 from CMG2451

| Strain | Genotype | Derivation[a] |
|---|---|---|
| CMG2451 | see Table 1 | disclosed in detail in WO 01/02580 |
| CMG2532 | NA7623 zff-208::Tn10 | zff-208::Tn10 from CAG18481[b] |
| CMG2533 | CMG2451 ndk::kan | ndk::kan zff-208::Tn10 from CMG2532 |
| | zff-208::Tn10 | |
| CMG2549 | CMG2533 λTn10 tet[S] | Tn10 deletion of CMG2533 and tet[Sc] |
| CMG2560 | CMG2549/pCG195 λ⁻ nic⁺ bio⁺ | P1 transduction CMG2549/pCG195 to nic⁺ & bio⁺ |
| CMG2576 | CMG2560/pCG596 thyA748::Tn10 | thyA748::Tn10 from KL742 (CGSC6212[d]) |

[a]Mutations were introduced into E. coli strains by phage P1 transduction. If the mutation has a selective marker, direct P1 transduction was used. If the mutation has no selective marker, P1 co-transduction with the nearby Tn10 insertion was used.
[b]Singer et al. Microbiol. Rev. 53: 1-24, 1989.
[c]Tn10 deletion was generated by growing E. coli strain on chlortetracycline medium (Maloy & Nunn J. Bacteriol. 145: 1110-1112, 1981.)
[d]All CGSC strains can be obtained for E. coli Genetic Stock Center, Yale University, PO. Box 208104, New Haven, CT 06520-8104.

EXAMPLE 4

Development of Improved Construct, pCG609, from pCG532

The construct was modified through a series of steps as outlined below:

pCG532 pCG596 pCG609

Figure 7:
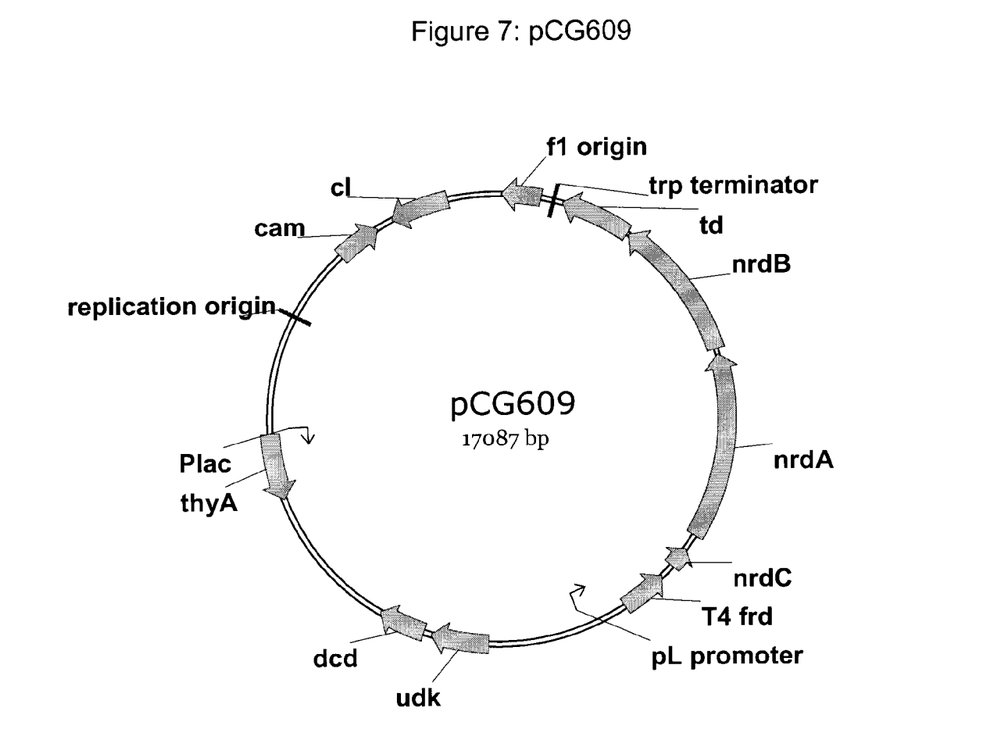
FIG. 7 illustrates a map for plasmid pCG609.
Figure 8:
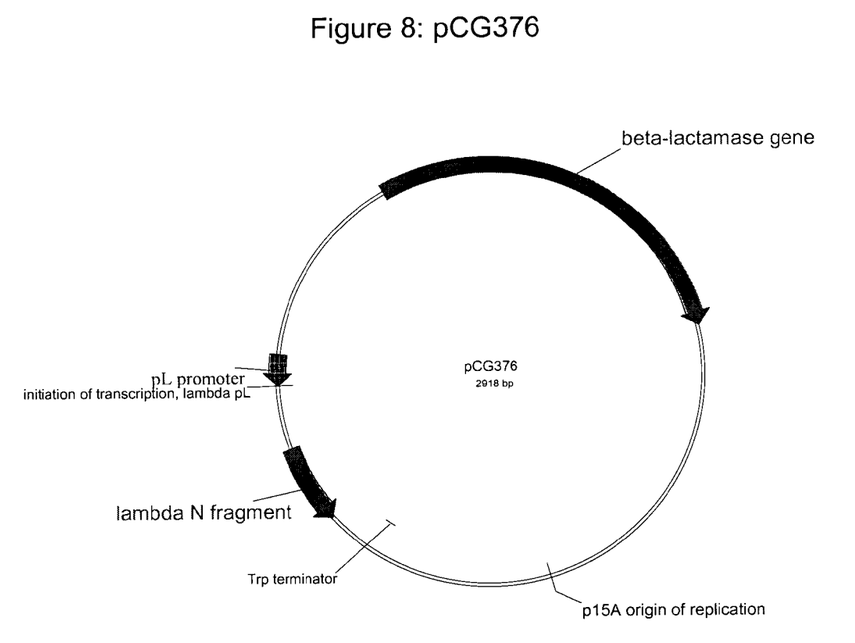
FIG. 8 illustrates maps for plasmid pCG376.

More specifically, the genes were derived as illustrated in Table 5 below. Plasmids pCG532 and pCG609 are illustrated by FIGS. 6 and 7 respectively, where the main features may be compared.

Of the three changes made to the construct only the T4 frd gene forms an essential part of one embodiment of the present invention. The effect of this modification is illustrated by Examples 6 and 7 below. The remaining changes were made to prevent loss of plasmid from the host strain, as detailed in Example 8 below.

TABLE 5

Development of pCG609 from Prior Art Construct pCG532

| Plasmid | Genes Added | Derivation |
|---|---|---|
| pCG532 | Prior art construct includes: T4 nrdCAB, td, (λ$P_L$ promoter) E. coli udk, dcd | disclosed in detail in WO 01/02580 |
| pCG590 | T4 frd cloned into pCG532 | T4 frd subcloned from pCG581 (see Example 5) |
| pCG596 | λ $cI_{857}$ cloned into pCG590 | moved from host strain chromosome |
| pCG609 | thyA cloned into pCG596 | native thyA of E. coli cloned by PCR |

EXAMPLE 5

Development of Test Constructs from pCG376

The effects of adding additional genes to established host strain/plasmid combinations were tested by introducing these on a second plasmid. The second plasmid is designed to be compatible with pCG532 and its derivatives, so that both may be stably maintained within a single E. coli host. pCG532 is ultimately derived from the natural plasmid ColE1: its detailed history is disclosed in WO 01/02580. The second plasmid is based on cloning vector pACYC177 (Chang & Cohen, J. Bacteriol. 134: 1141-1156, 1978), which is derived from natural plasmid p15A and compatible with ColE1.

This system has the advantage that gene additions may be tested without the need to further modify the already complex constructs described in Example 4 above. However, it is recognized that this system may be unstable without selective antibiotics and therefore not suited to large scale use in an industrial fermentation process.

The genes tested using the second plasmid are listed in Table 6 together with references reporting their entire nucleotide sequences. All were well characterised genes which were cloned by PCR according to standard protocols. Each was expressed from a bacteriophage lambda $P_L$ promoter so that it could be controlled with the $cI_{857}$ temperature sensitive repressor along with the cloned genes on the first plasmid and the dTMPase integrated into the host E. coli chromosome.

TABLE 6

Development of Test Constructs from pCG376

| Plasmid | Genes Added | Derivation/Reference |
|---|---|---|
| pCG376 | | disclosed in WO 01/02580 |
| pCG601 | glyA from *E. coli* K12 | Plamann et al., *Nucleic Acids Res.* 11: 2065-2075, 1983 |
| pCG844 | serA from *E. coli* K12 | Tobey & Grant, *J. Biol. Chem.* 261: 12179-12183, 1986 |
| pCG870 | ADE3 from *S. cerevisiae* | Staben & Rabinowitz, *J. Biol. Chem.* 261: 4629-4637, 1986 |
| pCG881 | fhs from *C. acidi-urici* | Whitehead & Rabinowitz, *J. Bacteriol.* 170: 3255-3261, 1988 |

EXAMPLE 6

Effect of Adding Cloned T4 frd Gene to Prior Art Host Strain/Construct pCG590, described in Example 4, differs from the prior art construct pCG532 only in the addition of the frd gene from bacteriophage T4, encoding T4 dihydrofolate reductase. The T4 enzyme is well characterised and readily expressed in *E. coli* (Purohit et al. *J. Biol. Chem.* 256: 9121-9125, 1981).

This gene was added to the "operon" expressed from the lambda $P_L$ promoter and is therefore induced with dTMPase (in the chromosome) and the T4 genes nrdc, nrdA, nrdB and td (on the plasmid) when temperature is increased and the lambda $cI_{857}$ repressor inactivated.

Using the method described in Example 2, shake flask data were obtained for the prior art host strain CMG2451 harbouring plasmid pCG590 and the result compared to those obtained in Example 2 with the same host and prior art plasmid pCG532. The results are given in Table 7 below.

TABLE 7

Shake Flask Average Specific Productivity (mg TdR/L/hr/g dry cell weight) for strains in enriched medium with and without the T4 frd gene expressed.

| Host Strain | Plasmid | Specific Productivity | % UdR | Comment |
|---|---|---|---|---|
| CMG2451 | pCG532 | 8.92 | 34.5 | data from Example 1 average of 23 experiments |
| | pCG590 | 9.43 | 7.02 | 590 = 532 + T4 frd gene average of 4 experiments |

What is apparent is that addition of the T4 frd gene greatly reduced the level of UdR produced, thereby simplifying production of substantially pure TdR by fermentation. It is expected that improved conversion of dUMP to dTMP rather than to UdR should result in additional thymidine as well as reduced UdR, which appears to be true in this case.

EXAMPLE 7

Effect of Adding Cloned T4 frd Gene to ndk Mutant Host Strain

Host strain CMG2549, described in Example 3, differs from the prior art host strain CMG2451 by a mutation in the ndk gene, encoding nucleoside diphosphate kinase. Mutation of this gene has been reported to increase intracellular pools of dCTP and dTTP in *E. coli* (Lu et al. *J. Mol. Biol.*, 254: 337-341, 1995). According to the principles taught in U.S. Pat. No. 5,213,972, the introduction of such a mutation in the pyrimidine deoxyribonucleoside biosynthetic pathway may be used to increase overall synthesis of TdR and UdR in an appropriately engineered organism.

Using the method of Example 2 shake flask data were obtained for the two host strains CMG2451 and CMG2549, each in combination with either pCG532 or pCG590. In this way the effects of the ndk mutation and the addition of T4 frd were compared both independently and in combination. The results are shown in Table 8 below.

TABLE 8

Shake Flask Average Specific Productivity (mg TdR/L/hr/g dry cell weight) for strains in enriched medium with or without ndk mutation and with or without cloned T4frd.

| Host Strain | Plasmid | Specific Productivity | % UdR | Comment |
|---|---|---|---|---|
| CMG2451 (ndk⁺) | pCG532 | 6.01 | 38.1 | Each result is the average of nine replicate shake-flasks. 12 hour results are shown because no detectable UdR could be measured for the pCG590 constructs at 6 hours (specific productivities are lower at 12 hours than at 6 hours) |
| | pCG590 (T4frd) | 6.67 | 10.2 | |
| CMG2549 (ndk⁻) | pCG532 | 11.44 | 36.7 | |
| | pCG590 (T4frd) | 19.64 | 1.48 | |

Surprisingly, the addition of T4 frd becomes even more effective in reducing UdR levels when introduced into an *E. coli* host carrying an ndk mutation.

Although the ndk mutation clearly increases the deoxyribonucleoside synthetic capacity of an *E. coli* strain according to the prior art, UdR content is too high for such an improvement to be exploited in the cost-effective production of pure thymidine. By providing an adequate supply of $CH_2$-THF according to the present invention, additional dUMP produced by the ndk mutant can be directed towards dTMP and thereby converted into thymidine, rather than converted into UdR. The result is a very substantial improvement over the prior art in terms of both thymidine productivity and low UdR content.

EXAMPLE 8

Effect of Plasmid Stabilisation on Thymidine Production

When the pCG590 was tested in host strain CMG2451 or its ndk mutant derivative CMG2549, the applicants observed plasmid loss as the resulting *E. coli* strain was cultured. This apparent instability was first addressed by relocating the phage lambda $cI_{857}$ temperature sensitive repressor from the chromosome (in host strain CMG2451 and its precursors) to the plasmid (in the construct pCG596 and its derivatives).

At temperatures of 31° C. and lower, the $cI_{857}$ repressor acts to prevent the expression of the dTMPase gene integrated into the chromosome, which was cloned with a lambda $P_L$ promoter. When the repressor is located on the plasmid, loss of that plasmid results in expression of dTMPase and consequent degradation of dTMP resulting in loss of viability for the plasmid-free cell. Using this principle, pCG596 was constructed as described in Example 4 and its host strain CMG2560 as in Example 3. When the resulting strain CMG2560/pCG596 was tested according to the shake-flask protocol of Example 2, a small increase was observed in rate of synthesis of thymidine relative to strain CMG2451/pCG590, as shown in Table 9.

However, the applicants determined that this mechanism was not completely effective in preventing loss of plasmid. It was discovered that plasmid loss with simultaneous mutation to inactivate the dTMPase gene resulted in the selection of viable, plasmid-free cells. An additional or alternative mechanism was required to ensure stable inheritance of the plasmid.

The thyA gene of E. coli, expressed from a lac promoter, was added to pCG596 to form pCG609. The chromosomal thyA gene could then be deleted in a host strain harbouring this plasmid. Expression of thymidylate synthase from thyA is essential for growth and survival because there is no other means by which the cell can synthesize dTMP. dTMP itself cannot pass through cell walls and "cross-feed" from thyA⁺ cells with plasmid to thyA cells having lost the plasmid. Such a mechanism, using an essential gene and a metabolite that does not cross feed, is particularly effective because genes can easily mutate to inactivate an enzyme activity, but much less readily recreate an activity that has been lost.

The construction of pCG609 is described in Example 4 and that of thyA⁻ host strain CMG2576 in Example 3. The resulting combination, strain CMG2576/pCG609, was tested according to the shake-flask fermentation protocol of Example 2 and a further small increase in thymidine production rate was observed relative to CMG2560/pCG596, as shown in Table 9.

TABLE 9

Shake Flask Average Specific Productivity (mg TdR/L/hr/g dry cell weight) for strains in enriched medium with and without genetic stabilisation of the plasmid.

| Host Strain | Plasmid | Specific Productivity | Comment |
| --- | --- | --- | --- |
| CMG2549 | pCG590 | 25.8 | Each result is the average of multiple replicate shake-flask tests, each of 6-8 flasks. 4-6 hour results are shown |
| CMG2560 ($\lambda^-$) | pCG596 ($\lambda$ cI$_{857}$) | 29.7 | |
| CMG2576 ($\lambda^-$, thyA) | pCG609 ($\lambda$ cI$_{857}$, thyA) | 31.8 | |

Figure 9:
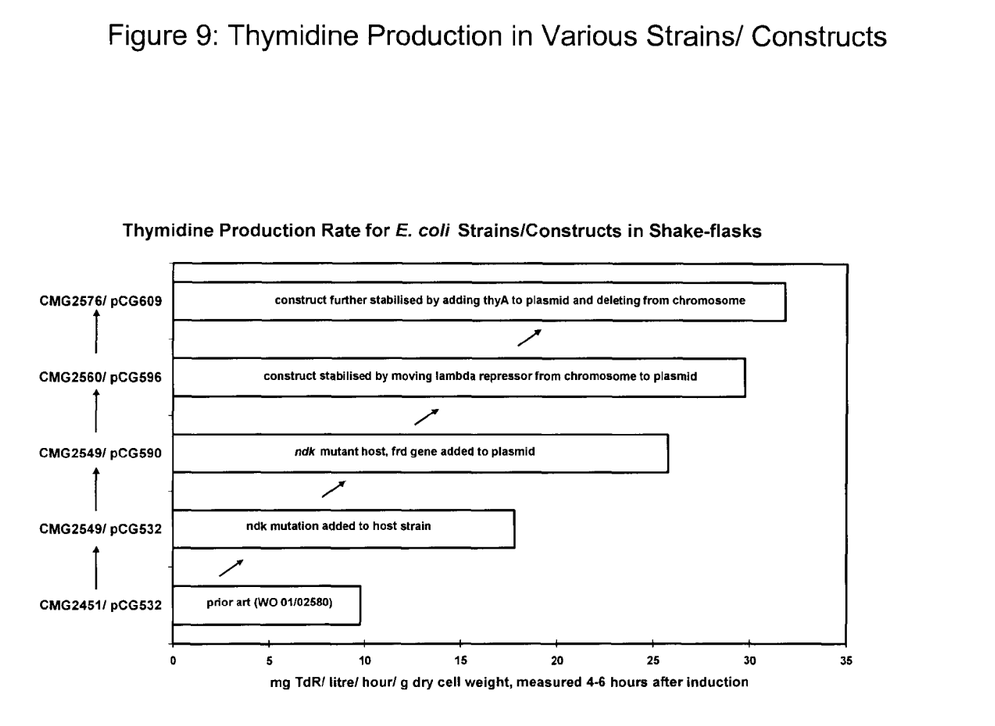
FIG. 9 compares thymidine production in a number of hosts/plasmids

These results are compared in FIG. 9 with the prior art strain CMG2451/pCG532 and its ndk mutant derivative. It can be seen that the benefits of the present invention in providing thymidine with low levels of UdR are enhanced by improved yields of thymidine when additional genetic material is provided in a form that will be stably maintained when the organism is cultured.

EXAMPLE 9

Effect of Adding Cloned glyA Gene

This example illustrates the effect of adding to the prior art construct and host strain a cloned E. coli glyA gene encoding serine hydroxymethyltransferase. This enzyme catalyses the conversion of serine to glycine coupled to the regeneration of CH$_2$-THF from THF (see FIG. 3). It will be recognized that the host strain already carries and expresses a glyA gene, and that the effect of this genetic modification is simply to boost the level of serine hydroxymethyltransferase when the plasmid-borne gene is expressed during temperature induction.

The glyA gene was cloned into plasmid vector pCG376, compatible with pCG532, as discussed in Example 5 above. The resulting plasmid pCG601 carries the glyA gene with a lambda P$_L$ promoter. Using the shake-flask test described in Example 2, CMG2451 harbouring both pCG532 and pCG601 was compared with the prior art CMG2451 harbouring pCG532 alone.

The results are given in Table 10, and may be compared with the results given in Example 6 showing the effect of adding T4 frd to the prior art host strain and construct. It is apparent that UdR is significantly reduced by the addition of an overexpressed glyA gene. However, the degree of reduction is less than that observed for T4 frd, and there is no significant increase in TdR.

TABLE 10

Shake Flask Average Specific Productivity (mg TdR/L/hr/g dry cell weight) for strains in enriched medium with and without the E. coli glyA gene overexpressed.

| Host Strain | Plasmids | Specific Productivity | % UdR | Comment |
| --- | --- | --- | --- | --- |
| CMG2451 | pCG532 | 8.92 | 34.5 | pCG376 is a cloning vector compatible with pCG532 pCG601 = pCG376 + glyA |
| | pCG532 + pCG601 | 8.79 | 22.07 | |

For the E. coli system used to demonstrate the present invention it could be concluded that the supply of CH$_2$-THF for conversion of dUMP to dTMP is limited by the rate of conversion of DHF to THF, rather than that of THF to CH$_2$-THF. This would explain why T4frd is much more effective in reducing UdR than is glyA. However, the relative effectiveness of the different approaches to achieve the goal of the present invention, that is an increase in the supply of CH$_2$-THF available to thymidylate synthase, is expected to be highly dependant upon the genetic background of the thymidine-producing organism to which this invention is applied.

It will be appreciated that the rate limiting step in CH$_2$-THF synthesis may be elsewhere in E. coli strains with different or additional added genes and mutations and in other thymidine-producing organisms. Indeed if the thymidine-producing organism continues to be improved according to the principles taught in U.S. Pat. No. 5,213,972 and WO 01/02580, then the rate limiting step may move to the serine hydroxymethyltransferase reaction and the addition of a cloned glyA gene show a more dramatic benefit in reducing the level of UdR in thymidine according to the principles of the present invention.

EXAMPLE 10

Effect of Adding Cloned serA Gene

This example illustrates the effect of improving the regeneration of CH$_2$-THF from THF by increasing the expression of an enzyme in the serine-glycine pathway (FIG. 3). 3-Phosphoglycerate dehydrogenase is the enzyme catalyzing the first step in this pathway, which is the major source of CH$_2$-THF in many organisms including E. coli. CH$_2$-THF is generated in two consecutive reactions: conversion of L-serine to glycine, catalysed by serine hydroxymethyltransferase, and conversion of glycine to carbon dioxide and water, catalysed by the glycine cleavage enzyme complex.

A cloned E. coli serA gene was added to increase the level of the native 3-phosphoglycerate dehydrogenase, using the second plasmid test system as detailed in Example 5. The starting point for this new genetic modification was the best mode host strain and construct CMG2576/pCG609 including the ndk mutation, T4 frd gene and genetically stabilised construct. It was reasoned that the benefit of increasing the capacity for synthesis of CH$_2$-THF from THF would be best tested in this background, where capacity for conversion of DHF to THF had been improved.

The serA gene was cloned into plasmid vector pCG376, as discussed in Example 5. The resulting plasmid pCG844 carries the serA gene with a lambda $P_L$ promoter. Using the shake-flask test described in Example 2, CMG2576 derivatives were compared, harbouring pCG609 combined with either pCG376 or pCG844. The results are given in Table 11.

There was no apparent change in the already very low ratio of UdR to TdR, but a slight increase in the rate of production of TdR. Compared with the effect of the T4 frd gene illustrated by Example 6, this improvement is relatively minor. However, it will be appreciated that the effect of adding the overexpressed serA gene could be more dramatic in an organism with a different genetic background producing higher levels of UdR.

Accumulation of L-serine is known to inhibit 3-phosphoglycerate dehydrogenase. However, in this example, this is not thought to be the case. Should however this occur, it would be preferable to modify the cloned serA gene since a single change in the amino acid sequence ($asn^{346}$ to ala) abolishes inhibition (Al-Rabiee et al., *J. Biol. Chem.* 271: 23235, 1997).

TABLE 11

Shake Flask Average Specific Productivity (mg TdR/L/hr/g dry cell weight) for strains in enriched medium with and without the *E. coli* serA gene overexpressed.

| Host Strain | Plasmids | Specific Productivity | % UdR | Comment |
|---|---|---|---|---|
| CMG2576 | pCG609 + pCG376 | 26.9 | 1.46 | pCG376 is a cloning vector compatible with pCG532 |
|  | pCG609 + pCG844 | 31.7 | 1.40 | pCG844 = pCG376 + serA |

EXAMPLE 11

Effect of Adding Cloned Yeast ADE3 Gene

This example illustrates the effect of adding to a thymidine-producing organism an additional pathway to provide regeneration of $CH_2$-THF. In the *E. coli* system chosen to exemplify the invention, regeneration of $CH_2$-THF using formate as the source of the required one-carbon unit is not a normal metabolic route. However, this mechanism exists in prokaryotes, including the yeast *Saccharomyces cerevisiae*, where a single gene may encode the trifunctional protein expressing the three enzyme activities required to convert THF to $CH_2$-THF by this route (see FIG. 4).

The applicants tested the effect of adding the ADE3 gene from yeast, encoding this trifunctional protein, to their combination of an ndk mutant *E. coli* host strain with a genetically stabilised construct including T4 frd. ADE3, with a lambda $P_L$ promoter, was cloned into pCG376 as described in Example 5, generating the construct pCG870.

In a shake-flask fermentation test using the Example 2 protocol, CMG2576 derivatives were compared harbouring either pCG609 alone or both pCG609 and pCG870. CGM2576 harbouring both pGC609 and the vector pCG376 was also included in the test to control for the effect of the second plasmid. Results are shown in Table 12 below. Although there is no significant effect on TdR productivity, UdR content has been reduced still further from an already very low level. It will be appreciated that, although the benefit is not dramatic in the genetic background of this example, it may be better realized in *E. coli* strains with different or additional added genes and mutations or indeed in other thymidine-producing organisms.

It will be further recognized that formate is not the normal source of one-carbon units for $CH_2$-THF in a prokaryotic organism such as *E. Coli*, hence this aspect of the invention may be require further genetic manipulation in order to have its maximum effect. For example the pyruvate formate lyase enzyme that generates formate from pyruvate could be overexpressed to increase the availability of formate for methylation of THF (see FIG. 5).

TABLE 12

Shake Flask Average Specific Productivity (mg TdR/L/hr/g dry cell weight) for strains in enriched medium with and without the yeast ADE3 gene expressed.

| Host Strain | Plasmids | Specific Productivity | % UdR | Comments |
|---|---|---|---|---|
| CMG2576 | pCG609 | 27.2 | 1.22 | 4-6 hour results. |
|  | pCG609 + pCG376 | 29.9 | 1.28 | pCG376 is a cloning vector compatible with pCG609 |
|  | pCG609 + pCG870 | 27.2 | 0.71 | pCG870 = pCG376 + ADE3 |

EXAMPLE 12

Effect of Adding Cloned *Clostridium acidi-urici* fhs Gene

This example illustrates an alternative mechanism to introduce into *E. coli* a pathway to regenerate $CH_2$-THF using formate. As shown in FIG. 4, three enzymes are required to catalyse this reaction. *E. coli* is unable to use this pathway because it lacks the first of these enzymes, formyltetrahydrofolate synthetase (EC 6.3.4.3). The remaining two enzymes are present as a bifunctional protein encoded by the folD gene.

As an alternative to the yeast ADE3 gene encoding all three enzyme activities, the applicants introduced into a thymidine-producing strain of *E. coli* the fhs gene of *C. acidi-urici*, which encodes only formyltetrahydrofolate synthetase, completing the set of enzymes required for the formate pathway. As for ADE3, this genetic change was tested in the best mode combination of host strain CMG2576 and construct pCG609 using a second plasmid vector.

fhs, with a lambda $P_L$ promoter, was cloned into pCG376 as described in Example 5, generating the construct pCG881. In a shake-flask fermentation test using the Example 2 protocol, CMG2576 derivatives were compared harbouring pCG609 together with either pCG881 or pCG376. Results are shown in Table 13 below.

In contrast with the ADE3 example above, there was no reduction in the already low level of UdR in this best mode strain and construct. However, there was an apparent slight increase in TdR productivity. As for the previous example, it will be appreciated that this is an aspect of the present invention that may be better realized in thymidine-producing organisms with different genetic backgrounds, or in combination with other changes affecting the availability of formate for conversion of THF to $CH_2$-THF.

TABLE 13

Shake Flask Average Specific Productivity (mg TdR/L/hr/g dry cell weight) for strains in enriched medium with and without the C. acidi-urici fhs gene expressed.

| Host Strain | Plasmids | Specific Productivity | % UdR | Comments |
|---|---|---|---|---|
| CMG2576 | pCG609 + pCG376 | 19.3 | 0.294 | 12 hour results, average of three experiments. |
| | pCG609 + pCG881 | 23.7 | 0.361 | pCG881 = pCG376 + fhs |

The invention claimed is:

1. A bacterium capable of producing thymidine when grown in a culture medium, the bacterium comprising one or more genetic modifications to its DNA, or some extra-chromosomal DNA necessary for its growth, characterized in that the bacterium comprises one or more genetic modifications which result in the thymidine biosynthetic pathway preferentially producing TdR at the expense of UdR as a consequence of one or more genetic modifications which increases the availability of a single carbon unit to dUMP for conversion to dTMP, wherein at least one genetic modification comprises introducing a transcriptional unit capable of expressing a dihydrofolate reductase (EC 1.5.1.3) and wherein the bacterium comprises a host strain and at least one construct comprising extra-chromosomal DNA and wherein a host strain gene encoding a nucleoside diphosphate kinase (EC 2.7.4.6) of the bacterium has been knocked out or otherwise inactivated or excised.

2. The bacterium as claimed in claim 1 wherein the host strain is stabilized such that if the one or more constructs are lost, the host bacterium is unable to make DNA and dies.

3. The bacterium as claimed in claim 1 wherein the dihydrofolate reductase is a T even phage dihydrofolate reductase.

4. The bacterium as claimed in claim 3 wherein the T even phage is T4.

5. The bacterium as claimed in claim 1 wherein the transcriptional unit is a frd gene.

* * * * *